US011229717B2

(12) United States Patent
Paris, Jr. et al.

(10) Patent No.: US 11,229,717 B2
(45) Date of Patent: Jan. 25, 2022

(54) SYSTEM AND METHOD FOR EFFECTIVE CLEANING AND DISINFECTING PROTOCOL

(71) Applicant: ANNIHILARE MEDICAL SYSTEMS, INC., Lincolnton, NC (US)

(72) Inventors: Marion E. Paris, Jr., Lincolnton, NC (US); Clay Parker Sipes, Conover, NC (US)

(73) Assignee: ANNIHILARE MEDICAL SYSTEMS, INC., Lincolnton, NC (US)

( * ) Notice: Subject to any disclaimer, the term of this patent is extended or adjusted under 35 U.S.C. 154(b) by 199 days.

(21) Appl. No.: 16/585,224

(22) Filed: Sep. 27, 2019

(65) Prior Publication Data

US 2021/0093741 A1 Apr. 1, 2021

(51) Int. Cl.
*A61L 2/24* (2006.01)
*H04W 4/80* (2018.01)
(Continued)

(52) U.S. Cl.
CPC ........ *A61L 2/24* (2013.01); *A61L 2/18* (2013.01); *H04W 4/33* (2018.02); *H04W 4/80* (2018.02); *H04W 4/029* (2018.02)

(58) Field of Classification Search
CPC .......... A61L 2/24; H04W 4/029; H04W 4/33; H04W 4/80
See application file for complete search history.

(56) References Cited

U.S. PATENT DOCUMENTS 8,204,620 B2 6/2012 Mallett et al.
9,051,163 B2 6/2015 Mehus et al.
(Continued)

FOREIGN PATENT DOCUMENTS

| CA | 2915815 C | 7/2018 |
| EP | 3316189 A1 | 5/2018 |
| WO | 2014204857 A1 | 12/2014 |

OTHER PUBLICATIONS

SSS Triple S Healthcare Solutions, Study Guide Cleaning and Disinfecting the Occupied Patient Room, Bridging The Gap Health Care Environmental Services Training Education and Developmental Series, 12 pages, Billerica, MA USA.

(Continued)

*Primary Examiner* — David Bilodeau
(74) *Attorney, Agent, or Firm* — Christopher C. Dremann, P.C.; Christopher C. Dremann

(57) ABSTRACT

A system and method for an effective cleaning and disinfecting protocol includes a portable computing device operable for wireless communications and having a machine-readable computer program. The system and method further includes a remote computing device operable for wireless communications and having a machine-readable computer program. The portable computing device wirelessly receives information in the form of digital data from at least one identification tag for use with the machine-readable computer program on the portable computing device to perform the cleaning and disinfecting protocol. The remote computing device wireless receives information in the form of digital data from the machine-readable computer program on the portable computing device for use with the machine-readable computer program on the remote computing device to verify the prescribed cleaning and disinfecting protocol has been properly performed.

16 Claims, 10 Drawing Sheets

(51) Int. Cl.
*A61L 2/18* (2006.01)
*H04W 4/33* (2018.01)
*H04W 4/029* (2018.01)

(56) References Cited

U.S. PATENT DOCUMENTS

| | | |
|---|---|---|
| 9,433,695 B2 | 9/2016 | Aamodt et al. |
| 9,679,170 B2 | 6/2017 | Paris, Jr. et al. |
| 10,521,765 B2 | 12/2019 | Paris |
| 10,885,497 B2 | 1/2021 | Paris |
| 2008/0190953 A1 | 8/2008 | Mallett et al. |
| 2011/0084835 A1* | 4/2011 | Whitehouse ............ A61B 1/121 340/540 |
| 2013/0015956 A1* | 1/2013 | Wegelin ................. G16H 40/20 340/10.1 |
| 2013/0122807 A1* | 5/2013 | Tenarvitz ............. H04B 5/0031 455/41.1 |
| 2014/0368318 A1* | 12/2014 | Paris, Jr ................... A61J 7/04 340/10.1 |
| 2017/0185930 A1* | 6/2017 | Perry ....................... H04L 67/26 |
| 2017/0286904 A1 | 10/2017 | Paris, Jr. et al. |
| 2019/0377399 A1* | 12/2019 | Cannell .................. G06F 1/263 |
| 2021/0161355 A1* | 6/2021 | Rahn ................... A47L 15/0015 |

OTHER PUBLICATIONS

Virox Technologies, Inc., Patient Room Cleaning and Disinfecting Protocol, 4 pages.

* cited by examiner

SYSTEM AND METHOD FOR EFFECTIVE CLEANING AND DISINFECTING PROTOCOL

FIELD OF THE INVENTION

The present invention relates generally to an improved system and method for an effective cleaning and disinfecting protocol. More particularly, the invention relates to a system and method for verifying that an effective cleaning and disinfecting protocol has been performed. In an advantageous embodiment, the invention is a system and method for verifying that a prescribed cleaning and disinfecting protocol has been performed by environmental services personnel at a healthcare facility using an effective disinfectant agent.

BACKGROUND OF THE INVENTION

Many facilities, including hospitals, nursing homes, prisons, schools and public terminals, are highly susceptible to multi-drug resistant organisms (MDROs), commonly referred to as infectious bacteria and viruses. For example, the Centers for Disease Control and Prevention (CDCP) estimates that infections acquired from healthcare and food service facilities kill more individuals each year than vehicle accidents, breast cancer or AIDS. As a result, the Environmental Protection Agency (EPA) and the Food and Drug Administration (FDA) prescribe effective cleaning and disinfecting procedures to be used in facilities that provide healthcare services and/or food services. In response, hospitals, nursing homes, prisons and schools have instituted detailed cleaning and disinfecting protocols along with intensive training programs for environmental services personnel to ensure that areas accessed by patients, staff and the public are clean and hygienic.

The aforementioned facilities, especially healthcare facilities, have historically utilized a variety of high, medium and low level disinfectants, including formaldehyde, hydrogen peroxide, peracetic acid and chlorine-releasing agents (CRAs), including sodium hypochlorite, iodophor and phenol solutions. More recently, Hypochlorous acid (HOCl) has been introduced as a more effective and environmentally friendly alternative to traditional disinfecting agents. Hypochlorous acid is a weak acid formed when chlorine dissolves in water and partially dissociates. Consequently, Hypochlorous acid acts as an oxidizer and a primary disinfecting agent in a chlorine solution. The beneficial characteristics attributed to Hypochlorous acid include that it is a highly effective disinfecting agent for destroying infectious bacteria and viruses, most notably *C. diff, E. Coli*, MRSA (Staph), Salmonella, Tuberculosis, Human Immunodeficiency Virus (HIV), and Severe Acute Respiratory Syndrome (SARS). Despite being highly effective, Hypochlorous acid is relatively harmless to humans at a concentration sufficient for effective cleaning and disinfecting. Consequently, Hypochlorous acid is an approved cleaning agent and disinfectant for use in hospitals, nursing homes, prisons, schools and public terminals.

Other cleaning and disinfectant agents commonly used in the aforementioned facilities are not as environmentally friendly or as effective as Hypochlorous acid in destroying harmful and deadly bacteria and viruses. As a result, it is not uncommon for individuals to contract serious illnesses from the bacteria and viruses at the aforementioned facilities that are cleaned with other disinfectants. The inability to effectively destroy infectious organisms increases healthcare costs and causes physical harm to individuals that could have been prevented with the use of the more effective Hypochlorous acid disinfectant agent.

Although highly effective, Hypochlorous acid has a limited lifespan of effectiveness as a disinfectant agent. Over time Hypochlorous acid decomposes to chloric acid, hydrochloric acid, and oxygen; none of which separately exhibit the same desirable disinfectant properties as Hypochlorous acid. The lifespan of effectiveness for Hypochlorous acid as a disinfectant agent is typically around thirty (30) days from the time it is produced. Consequently, it is imperative to take steps to ensure that an effective Hypochlorous acid disinfectant solution is being used by environmental services personnel in an established cleaning and disinfecting protocol at facilities such as hospitals, nursing homes, prisons, schools and public terminals. In particular, it is essential that environmental services personnel use a Hypochlorous acid disinfectant solution within its thirty (30) day lifecycle of effectiveness.

U.S. Pat. No. 9,679,170 assigned to Prime ITS of Houston, Tex., USA discloses a system and method for monitoring the distribution a disinfectant agent having an expiration, such as a Hypochlorous acid disinfectant solution, and tracking its volume use as a disinfectant solution. The system and method taught by the patent ensures that a disinfectant solution in a container is within its allocated expiration by tracking the physical container itself and monitoring the volume of the disinfectant solution in the container. However, the Prime ITS system and method does not verify that an effective cleaning and disinfecting protocol has been performed, or provide the functionality necessary to satisfy EPA and FDA compliance and reporting requirements for a prescribed cleaning and disinfecting protocol.

A cleaning and disinfecting protocol using Accelerated Hydrogen Peroxide (AHP) is disclosed in a white paper available from Virox™ Technologies, Inc. of Ontario, Canada entitled "Patient Room Cleaning And Disinfection Protocol." Another cleaning and disinfecting protocol for use by environmental services personnel at healthcare facilities is disclosed in a study guide published by SSS® Triple S Healthcare Solutions of Billerica, Mass. entitled "Cleaning and Disinfecting the Occupied Patient Room." The SSS® study guide teaches that a proper cleaning and disinfecting process assists in preventing cross-transmission of MDROs among patients, staff and visitors through contact with contaminated surfaces in a patient room. The SSS® study guide provides environmental services personnel with education and training regarding cleaning cart set-up, work scheduling, and safety procedures consistent with performing an effective cleaning and disinfecting protocol. Nevertheless, additional measures must be implemented to verify that the environmental services personnel have actually adhered to the prescribed cleaning and disinfecting protocol to satisfy EPA and FDA compliance and reporting requirements.

In view of the foregoing, it is apparent a need exists for an improved system and method for an effective cleaning and disinfecting protocol. A more particular need exists for a system and method for verifying that an effective cleaning and disinfecting protocol has been performed. Furthermore, a specific need exists for a system and method for verifying that a prescribed cleaning and disinfecting protocol has been performed by environmental services personnel at a healthcare facility using a disinfectant agent within its lifecycle of effectiveness. Such a system and method for an effective cleaning and disinfecting protocol advantageously includes features of data management, tracking, analysis and reporting functionality to satisfy EPA and FDA compliance and reporting requirements.

Certain aspects, objects, features and advantages of the invention will be made apparent, or will be readily understood and appreciated by those skilled in the relevant art, with reference to the exemplary embodiments of the invention described herein and shown in the accompanying drawing figures. It is intended that the certain aspects, objects, features and advantages of the invention set forth herein be encompassed by the ordinary and customary meaning of the elements, terms and limitations of the appended claims given their broadest reasonable interpretation and construction within the context of this disclosure. Some or all aspects, objects, features and advantages of the invention, as well as others not expressly or inherently disclosed herein, may be accomplished by one or more of the exemplary embodiments described and shown in the accompanying drawing figures. However, it should be appreciated that the written description and drawing figures are for illustrative purposes only, and that many modifications, substitutions or revisions may be made to the exemplary embodiments without departing from the general concepts of the invention and the intended scope of the appended claims as broadly interpreted and properly construed.

BRIEF DESCRIPTION OF THE DRAWINGS

The aforementioned aspects, objects, features and advantages of the invention will be more fully understood and appreciated when considered with reference to the accompanying drawing figures, in which like reference characters designate the same or similar parts throughout the several views.

DETAILED DESCRIPTION OF EXEMPLARY EMBODIMENTS OF THE INVENTION

Figure 1:
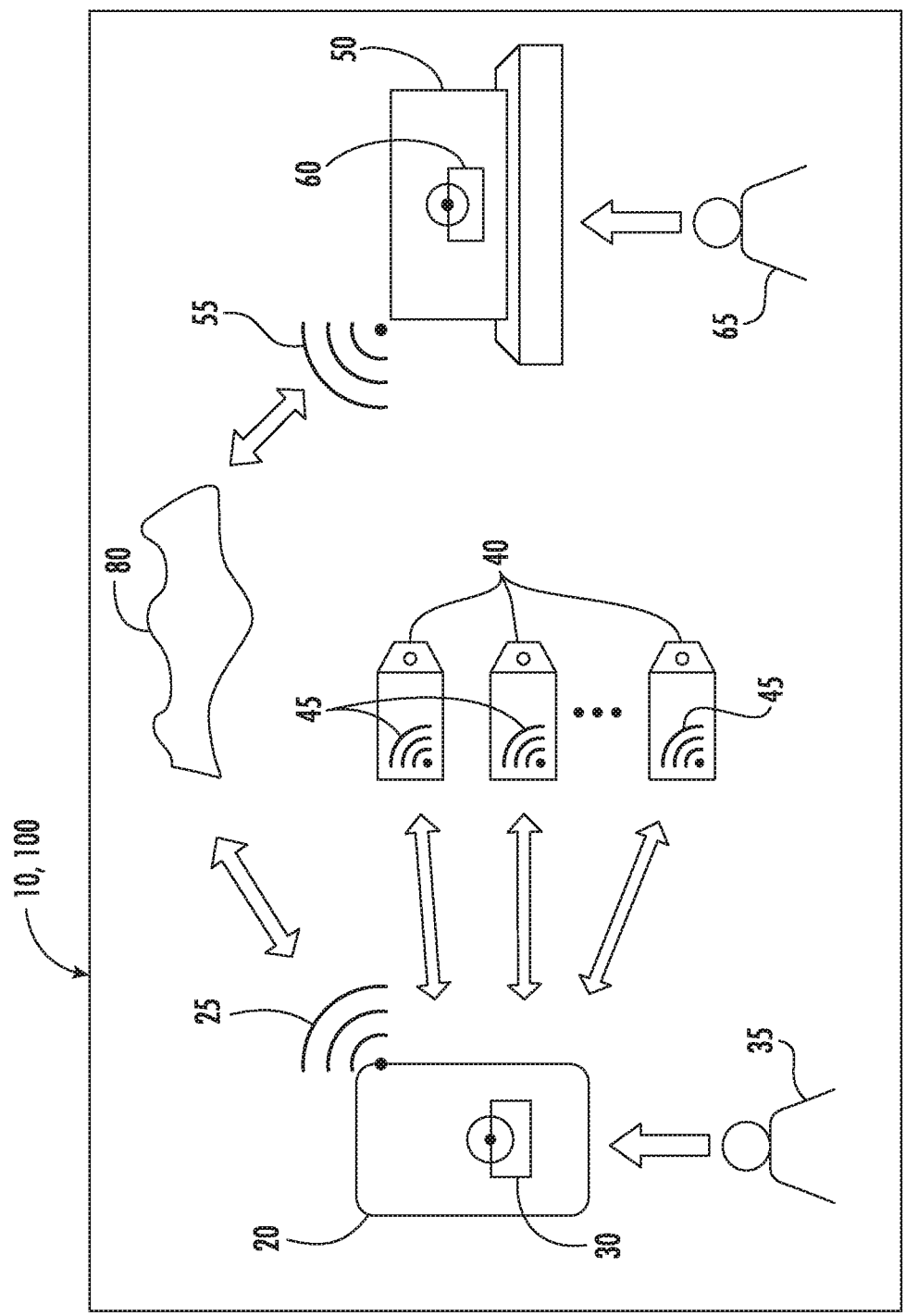
FIG. 1 shows a schematic diagram illustrating an exemplary embodiment of an improved system and method for an effective cleaning and disinfecting protocol according to the present invention.

Exemplary embodiments of the present invention are described hereafter and shown in the accompanying drawing figures. The embodiments described and shown herein are directed to an improved system, indicated generally by reference character 10, and an improved method, indicated generally by reference character 100, for an effective cleaning and disinfecting protocol. In general, the system 10 and method 100 may be used to create, communicate, perform, monitor, update, track, analyze, verify and/or report any process, procedure, protocol or the like. Advantageous embodiments of the system 10 and method 100 are used to create, communicate, perform, monitor, update, track, analyze, verify and/or report a prescribed cleaning and disinfecting protocol. Various aspects, objects, features and advantages of the present invention are illustrated by exemplary embodiments of a system 10 and an associated method 100 for verifying that an effective cleaning and disinfecting protocol has been performed by authorized environmental services personnel. As will be described in greater detail, a particularly advantageous embodiment of the system 10 and method 100 verify that a prescribed cleaning and disinfecting protocol has been performed by environmental services personnel at a healthcare facility using an effective disinfectant agent, such as a Hypochlorous acid disinfectant solution.

As best illustrated with reference to the schematic diagram of FIG. 1, the system 10 generally comprises a portable computing device 20 operable for wireless communication 25 and for executing a machine-readable computer program 30 resident on the portable electronic device 20. In one embodiment, the computer program 30 enables an effective cleaning and disinfecting protocol to be performed by authorized environmental services personnel. The system 10 further comprises at least one identification tag 40 operable for wireless communication 45 with the portable computing device 20. System 10 further comprises a remote computing device 50 operable for wireless communication 55 and for executing a machine-readable computer program 60 resident on the remote computing device 50. In one embodiment, the computer program 60 enables an administrator 65 to manage the effective cleaning and disinfecting protocol. The remote computing device 50 may be further operable for wireless communication 55 with the at least one identification tag 40 to, for example, program the tag 40 with identifying information.

In one aspect of the system 10 and method 100, the administrator 65 executes the computer program 60 on the remote computing device 50 to create and store in memory at least one prescribed cleaning and disinfecting protocol. Each prescribed cleaning and disinfecting protocol is provided to the computer program 30 on the portable computing device 20 by means of wireless communication 55, 25 between the remote computing device 50 and the portable computing device 20, respectively. In an advantageous embodiment, wireless communication 55, 25 between computing device 50 and computing device 20 is accomplished via a computer network 80. The user 35 utilizes the portable computing device 20 to execute the computer program 30 and to obtain (i.e. read) information in the form of digital data from the at least one identification tag 40. The digital data from the identification tag 40 is stored in the computer program 30 on the portable computing device 20 and is accessed for use with the method 100 in a manner to be described hereafter. User 35 then enters additional information relating to the prescribed cleaning and disinfecting protocol into the computer program 30 on the portable computing device 20. The digital data from the identification tag 40 and the additional information from the computer program 30 on the portable computing device 20 are transmitted via wireless communication 25, 55 from the portable computing device 20 to the remote computing device 50 and stored in the computer program 60 on the remote computing device 50. The administrator 65 accesses the information from the computer program 60 to verify that the prescribed cleaning and disinfecting protocol has been performed by the user 35. The administrator 65 may also utilize the computer program 60 on the remote computing device 50 to perform monitoring, tracking, data management, analysis and/or, reporting functions, for example to satisfy EPA and FDA compliance and reporting requirements.

In an advantageous embodiment, system 10 comprises a portable computing device 20 operable for wireless communication 25 with at least one identification tag 40 and with a remote computing device 50. By way of example and not limitation, the computing device 20 may be a laptop computer, a tablet computer, an electronic personal data assistant (PDA) or a personal "Smart" device, such as a "Smartwatch" or "Smartphone." As used herein, the term "Smart" is intended to mean that the portable computing device 20 is capable of wirelessly receiving and transmitting digital data communications via a computer network 80, such as a local area network (LAN) or a global computer network (e.g., the Internet). For purposes of illustrating exemplary embodiments of a system 10 and method 100 for an effective cleaning and disinfecting protocol, the computing device 20 is preferably a conventional tablet computer or Smartphone having a resident machine-readable computer program 30. The portable computing device 20 is provided to at least one user 35, and in particular, to one or more environmental services personnel 35 responsible for cleaning and disinfecting an area or a room of a private or public facility. One or more computing devices 20 may be provided for use by all of the environmental services staff, or alternatively, each individual of the environmental services staff may be provided with a personal portable computing device 20.

Figure 2:
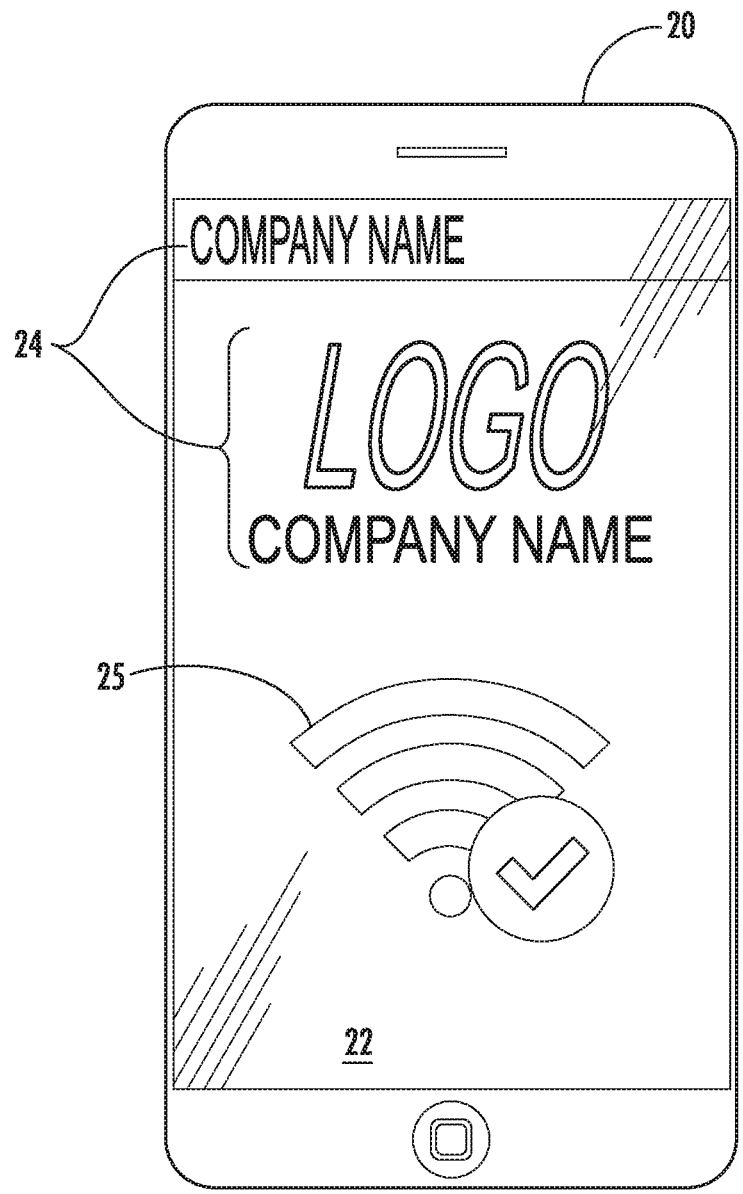
FIG. 2 shows an exemplary embodiment of a portable computing device for use with the system and method of FIG. 1.

Regardless, portable computing device 20 has a microprocessor and memory operable for receiving, storing and executing the machine-readable computer program 30 resident on the computing device 20. In the exemplary embodiments of the system 10 and method 100 described herein and shown in the accompanying drawing figures, computing device 20 is a conventional Smartphone, and the machine-readable computer program 30 is in the form of a mobile computing application, commonly referred to as a "mobile app." The mobile app 30 in turn is operable for wirelessly receiving, storing, displaying, executing, and wirelessly transmitting digital data. As best illustrated by FIG. 2, portable computing device 20 has a display screen 22 configured to display indicia 24 in the form of alphanumeric characters, symbols, logos, icons, graphical user interfaces (GUIs) and the like. The display screen 22 of the device 20 is further configured for a user 35 to interact with the indicia 24 in a conventional manner, for example by indicating a selection or inputting data using an input interface, such as a keyboard, keypad, tactile touchpad, touch screen or the like.

The portable computing device 20 may be programmed to provide secure user authentication and authorization, for example by means of a personal log-in screen requiring a username and password. The user authentication and authorization may be initiated upon powering the portable computing device 20, or alternatively, upon starting the mobile app 30 resident on the device 20. In this manner, one or more authorized individuals are able to use the same or different portable computing device 20, while unauthorized individuals are prevented from using the portable computing device 20 without providing proper authentication and authorization. The user authentication and authorization also provides the remote computing device 50 with an identification of the user 35. If desired, the indicia 24 on the display screen 22 of the computing device 20 may feature an identifier associated with the mobile app 30, such as a company name, a logo, an icon or a GUI that identifies a cleaning and disinfecting protocol and/or the facility to be cleaned and disinfected.

Figure 3:
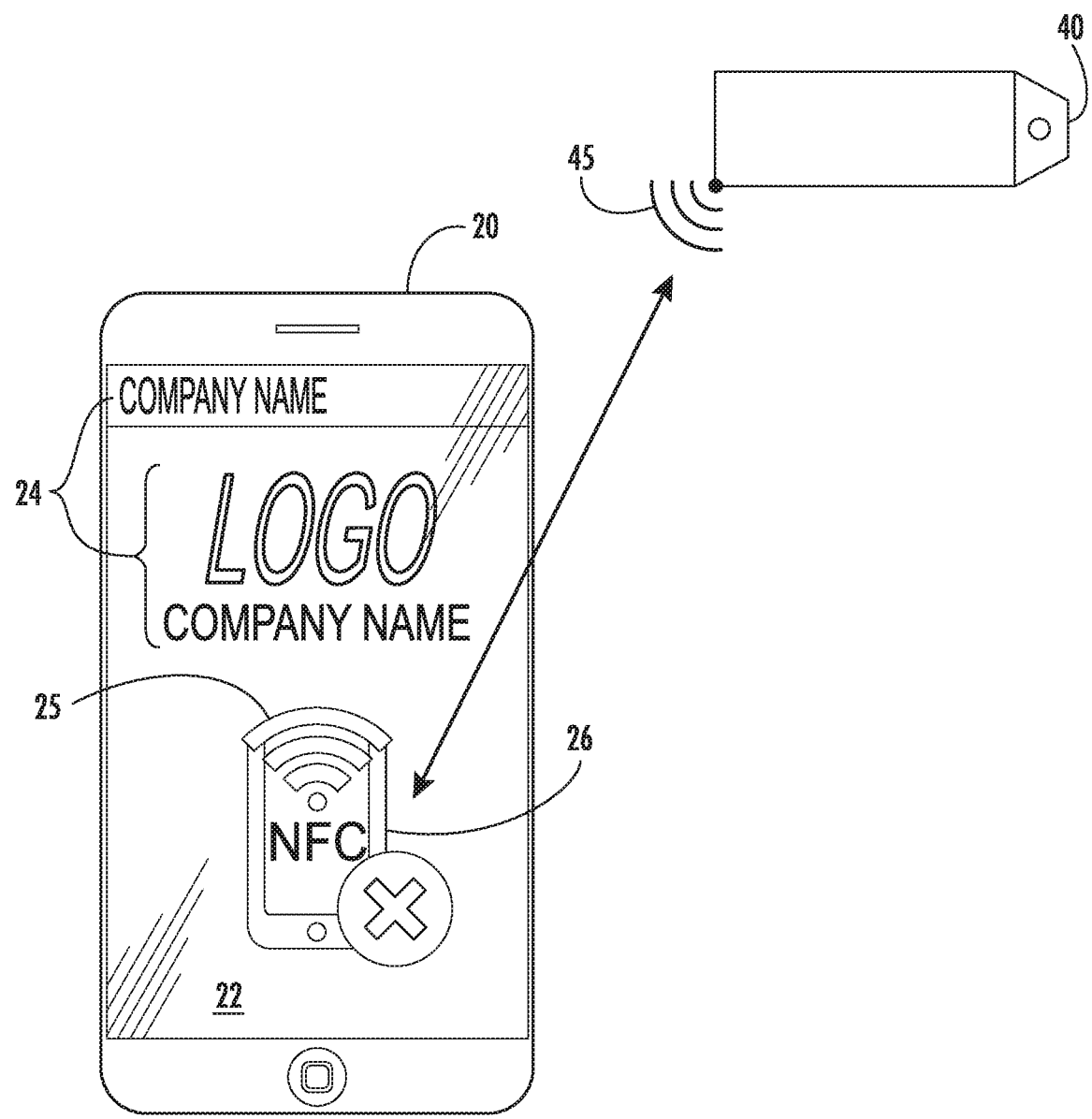
FIG. 3 shows a reader provided on the portable computing device of FIG. 2 for reading information from an electronic identification tag.

The portable computing device 20 further has a network interface card, network interface controller or network adapter, and associated software that is configured for the wireless communications 25 with the remote computing device 50 by means of the computer network 80. As best illustrated by FIG. 3, the computing device 20 is provided with a reader 26 for reading (i.e. receiving) information in the form of digital data from the at least one identification tag 40. Preferably, reader 26 acquires the digital data from an identification tag 40 by means of wireless communications 25, 45 between the portable computing device 20 and the identification tag 40. By way of example and not limitation, reader 26 may be in the form of a radio frequency identification (RFID) reader, an optical scanner having optical character recognition (OCR) capability, a bar code reader, a magnetic strip reader, a QR Code® (Quick-Response Code) reader, an electromagnetic radiation reader, a near field communication (NFC) reader or the like. The identification tag 40 may be an active device or a passive device, and comprises at least a means for generating electrical power and an electrical circuit board or "chip" for wirelessly transmitting information in the form of digital data. Accordingly, identification tag 40 may also be referred to herein as "electronic information tag 40' or "electronic identification tag. 40."

In a particularly advantageous embodiment, the reader 26 is a near field communication (NFC) transceiver operable for activating an NFC identification tag 40 and receiving a wireless transmission of digital data from the identification tag 40. The digital data acquired from the identification tag 40 is stored in the portable computing device 20 memory and provided to the mobile app 30 on the computing device 20. Reader 26 may also be operable for activating the NFC identification tag 40 and sending (i.e. transmitting) a wireless transmission of digital data from the mobile app 30 to the identification tag 40. Regardless, the digital data acquired from the identification tag 40 may be the identification of an item, such as a cleaning cart, or may be the identification of a location, such as an area or a room at a private or public facility to be cleaned and disinfected.

Alternatively or in addition, the digital data acquired from the identification tag 40 may include information to be processed by the mobile app 30 on the portable computing device 20 and/or the computer program 60 on the remote computing device 50.

By way of example and not limitation, the identification tag 40 may transmit digital data relating to the contents of a cleaning cart or to the location and status (e.g. occupied, unoccupied, exited, cleaned, etc.) of a patient room at a healthcare facility. Conversely, the administrator 65 may execute the computer program 60 on the remote computing device 50 to enter, store and wirelessly transmit such digital data to the mobile app 30 on the portable computing device 20 and/or to the identification tag 40. A unique feature of the provisioning functionality of the identification tag 40 is the ability to re-assign, re-allocate and/or to re-connect the digital data programmed (e.g., encoded) on the identification tag 40 and stored in the database of the computer program 60 on the remote computing device 50, using only the mobile app 30 provided on the portable computing device 20. If an identification tag 40 is removed, discarded, destroyed or moved to another item or location, the historical digital data of the identification tag 40 will not be lost for that item or location. This is because the system 10 and method 100 allocates and assigns a unique identification number (e.g., serial number or serial code) to each identification tag 40. Thus, a new identification tag can replace the missing identification tag 40 and be associated with the digital data relating to its item or location using the mobile device 20 by re-assigning and programming the unique identification number of the missing identification tag 40 to the replacement identification tag 40 and changing the relationship of the digital data and the unique identification number in the database. The secure database retains the identification number of the original identification tag 40 along with the historical digital data relating to the item or location so that the computer program 60 maintains a seamless history of cleaning and disinfecting protocols performed for verification to satisfy mandatory EPA and/or FDA compliance and reporting requirements.

As best illustrated with reference to the schematic diagram of FIG. 1, the method 100 utilizes the system 10 to verify that an effective cleaning and disinfecting protocol has been performed. In a particularly advantageous embodiment, the method 100 verifies that a prescribed cleaning and disinfecting protocol has been performed by environmental services personnel at a healthcare facility using an effective disinfectant agent, such as a Hypochlorous acid disinfectant solution. As previously described and depicted in FIG. 1, a remote computing device 50 operable for wireless communications 55 and having a machine-readable computer program 60 resident on the remote computing device 50 is provided for an administrator 65 of a prescribed cleaning and disinfecting protocol. Likewise, a portable computing device 20 operable for wireless communications 25 and having a machine-readable computer program in the form of a mobile app 30 resident on the portable computing device 20 is provided for a user 35 to perform the prescribed cleaning and disinfecting protocol. As previously mentioned, user 35 is one or more of the environmental services personnel at a facility required to be cleaned and disinfected, and the portable computing device 20 is operable for wireless communications 25, 55 with the remote computing device 50 by means of a computer network 80, such as a Local Area Network (LAN) or the Internet.

In an exemplary embodiment of the method 100, an administrator 65 executes the computer program 60 to create a prescribed cleaning and disinfecting protocol. By way of example and not limitation, the cleaning and disinfecting protocol may include a first check list of the items and quantities of materials required on a cleaning cart, and a second check list of the tasks that need to be performed for the prescribed cleaning and disinfecting protocol. If desired, the prescribed cleaning and disinfecting protocol may further include detailed instructions for properly performing the tasks of the cleaning and disinfecting protocol. Regardless, administrator 65 utilizes the remote computing device 50 to transmit information relating to the prescribed cleaning and disinfecting protocol in the form of digital data to the portable computing device 20 by means of wireless communications 55, 25 between the remote computing device 50 and the portable computing device 20. The digital data includes the prescribed cleaning and disinfecting protocol, as well as any other instructions and/or information that the administrator 65 deems necessary to provide to the user 35, such as general safety tips and/or notices regarding any restrictions or conditions at the facility. By way of example and not limitation, administrator 65 may need to advise user 35 that a certain area of the facility is restricted from access due to maintenance, repair, closure, etc. The digital data transmitted by the remote computing device 50 is stored in the memory of the portable computing device 20 and uploaded to the mobile app 30 provided on the portable computing device 20.

Figure 4:
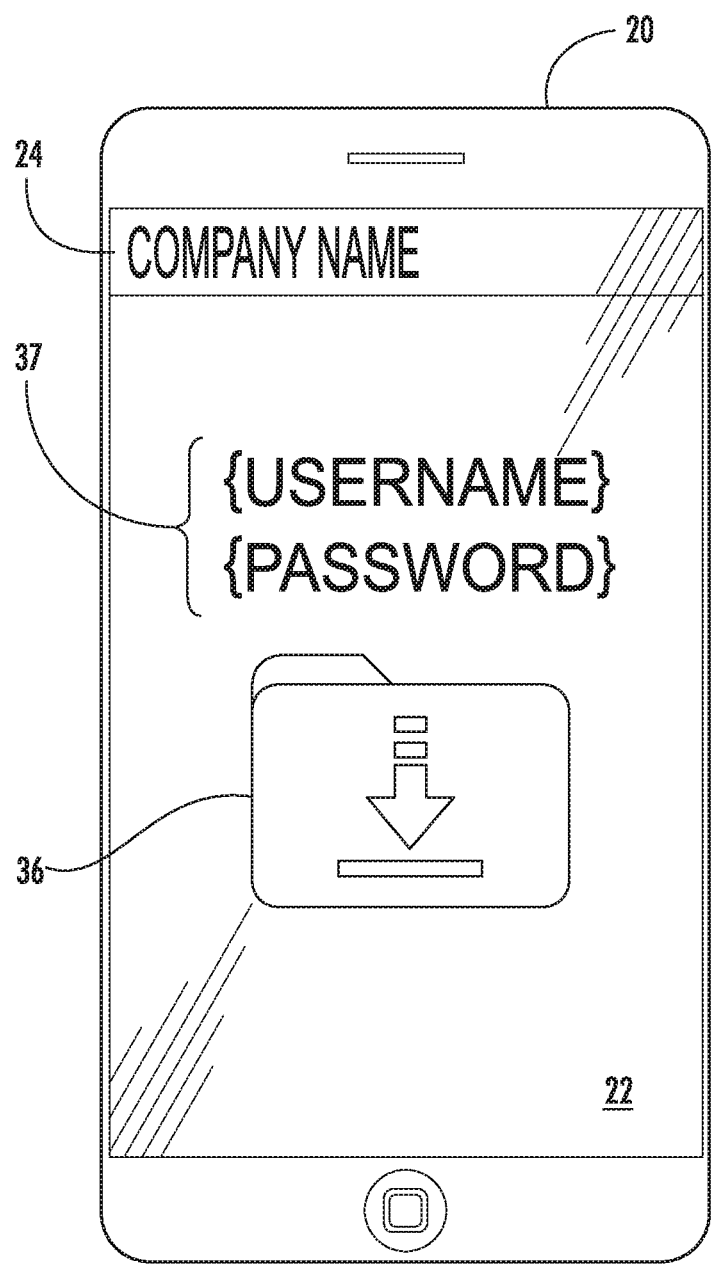
FIG. 4 shows an icon provided on the portable computing device of FIG. 2 for initiating a cleaning and disinfecting protocol, and an authentication and authorization log-in provided on the portable computing device for identifying a user of the cleaning and disinfecting protocol.
Figure 5:
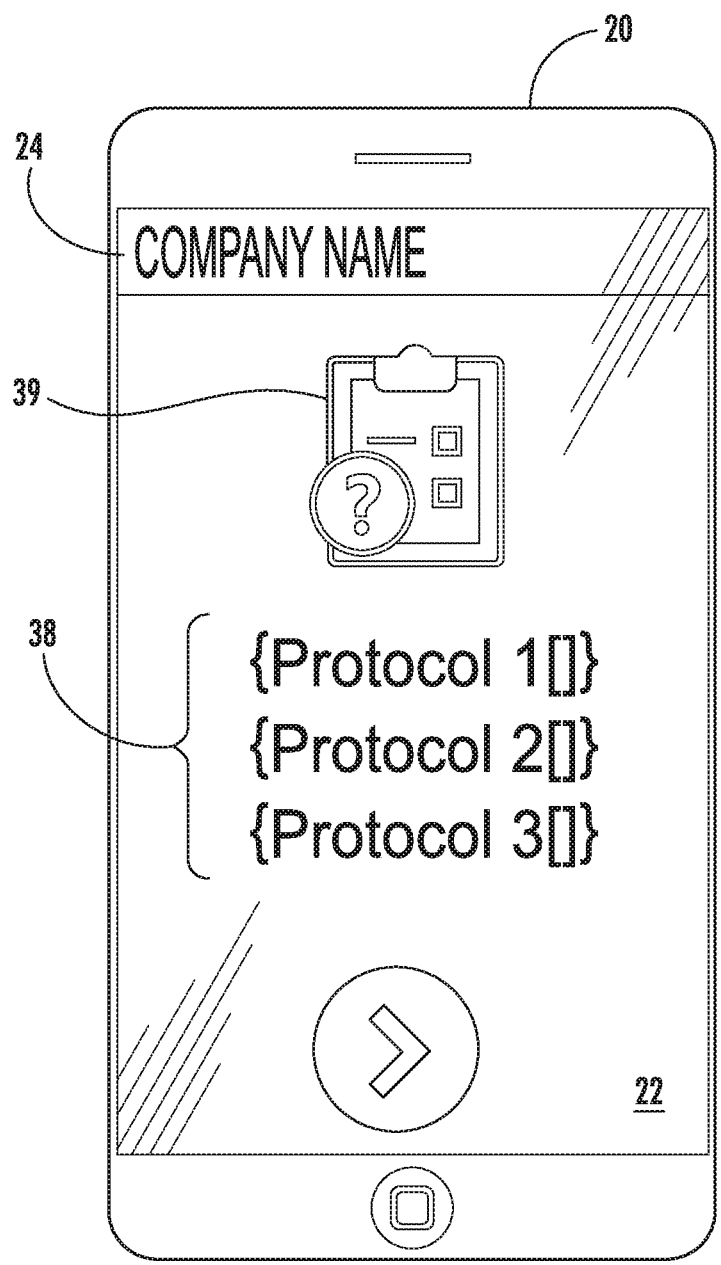
FIG. 5 shows a listing of available cleaning and disinfecting protocols provided on the portable computing device of FIG. 2.

As best illustrated by FIG. 4, the user 35 accesses the mobile app 30 on the portable computing device 20 in a conventional manner, for example by powering-up the computing device 20 or by selecting an icon 36, such as a graphical user interface (GUI), on a display screen 22 of the powered-up portable computing device 20. Preferably, access to the mobile app 30 requires some form of user authentication and authorization 37, for example a personal username and password. Once the mobile app 30 has been accessed (commonly referred to as "opened"), user 35 is able to view any instructions and/or information for the user 35 that the administrator 65 sent to the mobile app 30. As best illustrated by FIG. 5, the user 35 may need to select a prescribed cleaning and disinfecting protocol from a listing of available protocols 38 displayed on the display screen 22 depending on the particular type of cleaning and disinfecting to be performed, for example an occupied room, an unoccupied room, or an exited room that a patient has permanently vacated by being discharged or removed.

Regardless, user 35 activates the prescribed cleaning and disinfecting protocol 38 provided to the portable computing device 20 by the remote computing device 50. In general, the user 35 makes selections and enters information into the mobile app 30 using the display screen 22 on the portable computing device 20 as the user 35 performs the prescribed cleaning and disinfecting protocol 38. The selections and the information entered into the mobile app 30 by the user 35 are provided to the remote computing device 50 in the form of digital data by means of wireless communications 25, 55 between the portable computing device 20 and the remote computing device 50 via the computer network 80. The administrator 65 may then execute functions of the computer program 60 on the computing device 50 to monitor, track, store, display, manage, analyze, verify and/or report the information obtained from the mobile app 30. In particular, the administrator 65 uses the computer program 60 and the digital data from the mobile app 30 to verify that the prescribed cleaning and disinfecting protocol 38 has been performed, for example to satisfy mandatory EPA and/or FDA compliance and reporting requirements or for internal reporting purposes.

In a particularly advantageous embodiment of the method 100, user 35 is first required to confirm that an effective disinfectant agent is available to perform the prescribed cleaning and disinfecting protocol 38. As used herein, the term "effective disinfectant agent" is intended to mean that the cleaning and disinfectant solution to be used in the prescribed cleaning and disinfecting protocol 38 has not exceeded a predetermined acceptable time limit since the cleaning and disinfectant solution was produced to remain effective as a disinfectant, referred to herein as the "lifespan" or "lifecycle of the disinfectant solution." Any suitable disinfectant agent may be utilized with the system 10 and method 100. By way of example and not limitation, suitable cleaning and disinfectant solutions include formaldehyde, hydrogen peroxide, peracetic acid, chlorine-releasing agents (CRAs), such as sodium hypochlorite, iodophor and phenol solutions. Hypochlorous acid (HOCl) has been found to be a highly effective disinfectant agent for destroying infectious bacteria and viruses, most notably C. diff, E. Coli, MRSA (Staph), Salmonella, Tuberculosis, Human Immunodeficiency Virus (HIV), and Severe Acute Respiratory Syndrome (SARS), while being relatively harmless to humans at a sufficient disinfectant solution concentration. Consequently, Hypochlorous acid is a preferred disinfectant agent for use with the system 10 and the method 100 of the present invention.

As previously mentioned, Hypochlorous acid and other chlorine-based cleaning and disinfectant solutions have a limited lifespan of effectiveness as a disinfectant. Consequently, user 35 must first confirm that the cleaning and disinfectant solution (i.e., the Hypochlorous acid disinfectant agent) is within its lifecycle to be effective as a disinfectant. The user 35 may confirm that the cleaning and disinfectant solution, and in particular the Hypochlorous acid disinfectant agent, is effective in any suitable manner. For example, the user 35 may simply read a production date and/or an expiration date imprinted on a container of the cleaning and disinfectant solution that indicates whether the disinfectant agent is within its lifespan of effectiveness. The user 35 then manually inputs the production date and/or the expiration date into the mobile app 30. Alternatively, user 35 may scan a barcode, QR Code® or the like that indicates the date the cleaning and disinfectant solution was produced or will expire using the reader 26 provided on the portable computing device 20. Importantly, it is not necessary for the user 35 or the portable computing device 20 to monitor or track the amount of the cleaning and disinfectant solution in the container at any time, or to otherwise determine the volume of the cleaning and disinfectant solution used in any manner. It is only necessary for the user 35 or the mobile app 30 on the portable computing device 20 to confirm that the disinfectant agent in the container of cleaning and disinfectant solution to be used to perform the prescribed cleaning and disinfecting protocol is within the predetermined acceptable time limit to remain effective as a disinfectant agent. Alternatively or in addition, the user 35 may be required to identify the type of disinfectant agent and/or input an identifier, such as a lot number, serial number or the like from the container so that the effectiveness of the disinfectant agent can be confirmed by data stored within the mobile app 30 on the portable computing device 20 or within the computer program 60 on the remote computing device 50.

The prescribed cleaning and disinfecting protocol 38 selected from the mobile app 30 may next require user 35 to read a first identification tag 40 to obtain information in the form of digital data relating to an item or a location. As previously discussed, the user 35 may read the first identification tag 40 using the reader 26 provided on the portable computing device 20 in any suitable manner, for example with an optical scanner having optical character recognition (OCR) capability, a bar code reader, a QR Code® reader or the like. In a particularly advantageous embodiment, the prescribed cleaning and disinfecting protocol 38 requires the user 35 to read a first identification tag 40 associated with a cleaning cart (not shown) by means of a near field communication (NFC) transceiver 26 provided on the portable computing device 20. Regardless, the information from the first identification tag 40 is read into the mobile app 30 to determine the identity and/or the contents of the cleaning cart.

In one embodiment, the information obtained from the first identification tag 40 and provided to the mobile app 30 for the prescribed cleaning and disinfecting protocol 38 may comprise only an identifier, such as an identification number associated with the cleaning cart. In another embodiment, the information from the first identification tag 40 on the cleaning cart may further comprise an inventory of the contents of the cleaning cart. Regardless, the mobile app 30 may next require the user 35 to survey the contents of the cleaning cart to confirm that a sufficient amount of the cleaning supplies needed to properly perform the prescribed cleaning and disinfecting protocol 38 are available on the cleaning cart. By way of example, the mobile app 30 may require the user 35 to indicate by means of a check list whether a sufficient amount of the cleaning and disinfectant solution, cleaning rags, paper towels, clean linens and trash receptacle liners are available on the cleaning cart. In one embodiment, the user 35 indicates whether an item is available on the cleaning cart by selecting (e.g., tapping) a corresponding check box on the display screen 22 of the portable computing device 20. In the event that an inventory of the cleaning supplies available on the cleaning cart was obtained from the first identification tag 40, the mobile app 30 on the portable computing device 20 and/or the computer program 60 on the remote computing device 50 may compare the inventory of available cleaning supplies with the check list completed by the user 35 on the mobile app 30, for example as verification to satisfy mandatory EPA and/or FDA compliance and reporting requirements or for internal reporting purposes.

Once the user 35 has completed the check list to confirm that the necessary cleaning supplies are available on the cleaning cart, the mobile app 30 will permit the user 35 to continue to perform the prescribed cleaning and disinfecting protocol 38. By way of example and not limitation, the mobile app 30 may communicate to the remote computing device 50 that the user 35 is able to leave a designated area, such as a supply and staging area, to continue to perform the prescribed cleaning and disinfecting protocol 38. Alternatively or in addition, the mobile app 30 may display a message on the display screen 22 of the portable computing device 20 instructing the user 35 to continue to perform the prescribed cleaning and disinfecting protocol 38. Otherwise, the mobile app 30 indicates to the remote computing device 50 and/or portable computing device 20 that the check list of supplies needed to properly perform the prescribed cleaning and disinfecting protocol 38 has not been completed and approved.

Once the check list of cleaning supplies on the cleaning cart has been completed and approved, the user 35 proceeds to the first area or room to be cleaned and disinfected using the prescribed cleaning and disinfecting protocol 38. In one embodiment, a second identification tag 40 is provided at the location to be cleaned and disinfected using the prescribed cleaning and disinfecting protocol 38. Similar to the first identification tag 40 on the cleaning cart, the second identification tag 40 at the location is read by means of the reader 26 provided on the portable computing device 20. The second identification tag 40 may be read in any suitable manner, for example as previously described with reference to the first identification tag 40. In a particularly advantageous embodiment, the second identification tag 40 is also read by means of a near field communication (NFC) transceiver 26 provided on the portable computing device 20. In one embodiment, the second identification tag 40 may comprise only an identifier of the location. In another embodiment, the second identification tag 40 may comprise further information relating to the current status of the location, for example an occupied room, an unoccupied room, or an exited room that a patient has permanently vacated by being discharged or removed. In yet another embodiment, the further information contained on the second identification tag 40 may include an inventory of the contents of the location, for example whether the area or room contains amenities such as a shower, bathtub, toilet, sink and/or windows required to be cleaned and/or disinfected.

Figure 6:
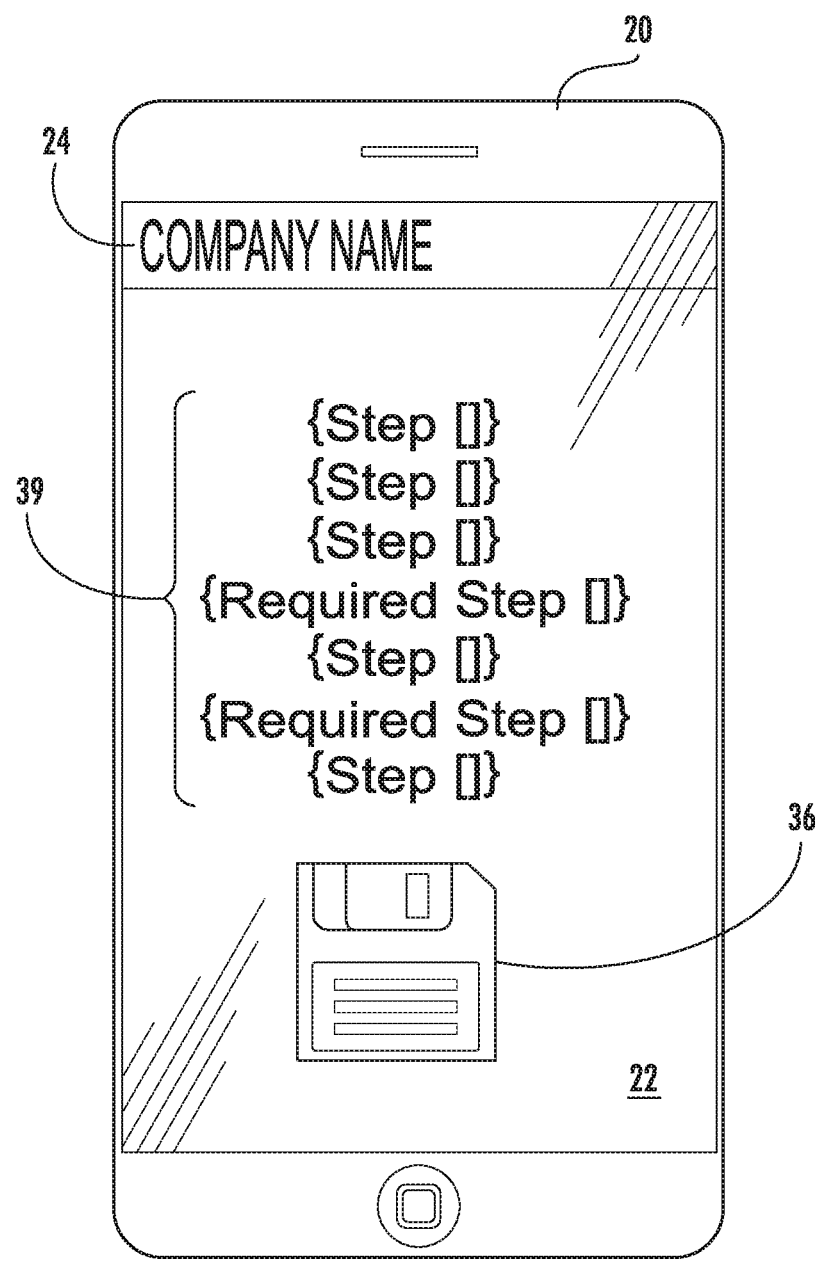
FIG. 6 shows a check list of instructions provided on the portable computing device of FIG. 2 for a user to perform a prescribed cleaning and disinfecting protocol.

As best illustrated by FIG. 6, the mobile app 30 next provides the user 35 with a check list 39 for cleaning and disinfecting the location identified by the second identification tag 40. By way of example and not limitation, the check list 39 may comprise detailed step-by-step instructions for cleaning and/or disinfecting a hospital room at a healthcare facility. For example, the check list 39 may prescribe instructions to remove trash, dust and remove soil load, change linens and/or curtains, disinfect high touch areas, sanitize food trays, and electro-statically apply a disinfectant agent, such as a Hypochlorous acid disinfectant solution, throughout the entire hospital room using an automated cart.

The machine-readable computer program 60 resident on the remote computing device 50 provides functionality that enables monitoring, compliance with standards, verification, reporting, and statistical analysis. As such, the computer program 60 can be used for investigative purposes to identify or rule out a possible source of infection. The system 10 and method 100 creates a prescribed cleaning and disinfecting protocol 38, communicates the prescribed cleaning and disinfecting protocol 38 to the user 35 through the mobile app 30 provided on the portable computing device 20, confirms that an effective cleaning and disinfectant solution is available for use, identifies and records the contents of a cleaning cart and a location to be cleaned and disinfected, monitors the activities and progress of the user 35, including the time spent by the user 35 performing the prescribed cleaning and disinfecting protocol 38 at the location, and verifies that the prescribed cleaning and disinfecting protocol 38 was properly performed and completed. In addition, the system 10 and method 100 tracks when a particular prescribed cleaning and disinfecting protocol 38 was created or updated, and by whom, as well as where (i.e., area or room of the facility) and when (i.e., date and time) a particular user 35 performed a prescribed cleaning and disinfecting protocol 38.

The system 10 and method 100 of the present invention provides the further advantage that a new cleaning and disinfecting protocol 38 can be created, or an existing cleaning and disinfecting protocol 38 can be updated, and prescribed to users 35 in real-time. By way of example and not limitation, If a cleaning and disinfecting protocol 38 needs to be created or updated due to a flu outbreak or an infection outbreak reported from another facility, an administrator 65 (such as a facility manager or an environmental services personnel supervisor) can rapidly create or update a cleaning and disinfecting protocol 38 in real-time using the computer program 60 provided on the remote computing device 50. In practice, the manager or supervisor utilizes an on-line control panel 70 (commonly known as and also referred to herein as a "dashboard") of the computer program 60 to program an executable job that automatically updates the identification number and/or the information of the affected identification tag(s) 40 when a user 35 executes the mobile app 30 on the portable computing device 20 so that the reader 26 (i.e., the NFC transceiver) wirelessly communicates with the identification tag 40. The administrator 65 can determine whether a global update is required or only specific identification tag(s) 40 need to be updated. This real-time capability of the system 10 and method 100 allows for a new or updated cleaning and disinfecting protocol 38 to be rapidly and instantaneously communicated to users 35 across the entire facility, and as such, is a significant improvement to traditional paper check lists and other communication methods.

The system 10 and method 100 of the present invention may also provide a notification function by means of the on-line dashboard 70 of the computer program 60 on the remote computing device 50. By way of example and not limitation, the dashboard 70 of the computer program 60 may include a platform 50 that utilizes code running in the background of a cloud-based application server. In one embodiment, the notification function issues a warning in the event a particular identification tag 40 has not been engaged (i.e., a user 35 has not caused the reader 26 of a portable computing device 20 to interrogate the identification tag 40) within a predetermined period of time established by the administrator 65 and monitored by a timer. The notification function ensures that each location (i.e., area or room of the facility) is processed with the prescribed cleaning and disinfecting protocol 38 in a timely manner to thereby prevent a possible infection. The notification function is both passive and active by nature and by choice. The warning issued by the notification function identifies each identification tag 40 and its unique identification number, along with the identity of the user 35 and the date and time the last prescribed cleaning and disinfecting protocol 38 was performed. The notification function accounts for the details of each occurrence to ensure that management can follow-up with adequate and appropriate inspections. The warning issued by the notification function cannot be resolved until the identification tag 40 of the item or location is engaged again and a prescribed cleaning and disinfecting protocol 38 is performed. Once the required action is properly performed and completed, the timer of the notification function is reset.

Figure 7:
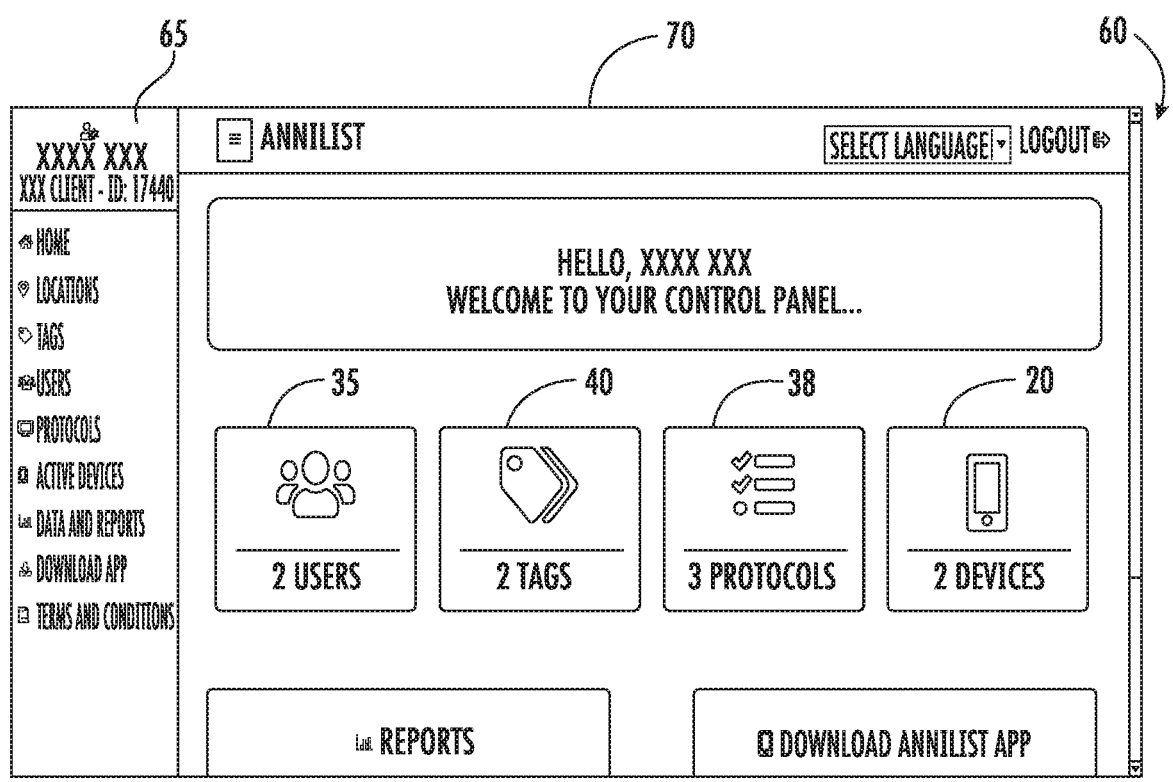
FIG. 7 shows a screenshot of an exemplary embodiment of a control panel of a computer program provided on a remote computing device for use by an administrator with the system and method of FIG. 1.
Figure 8:
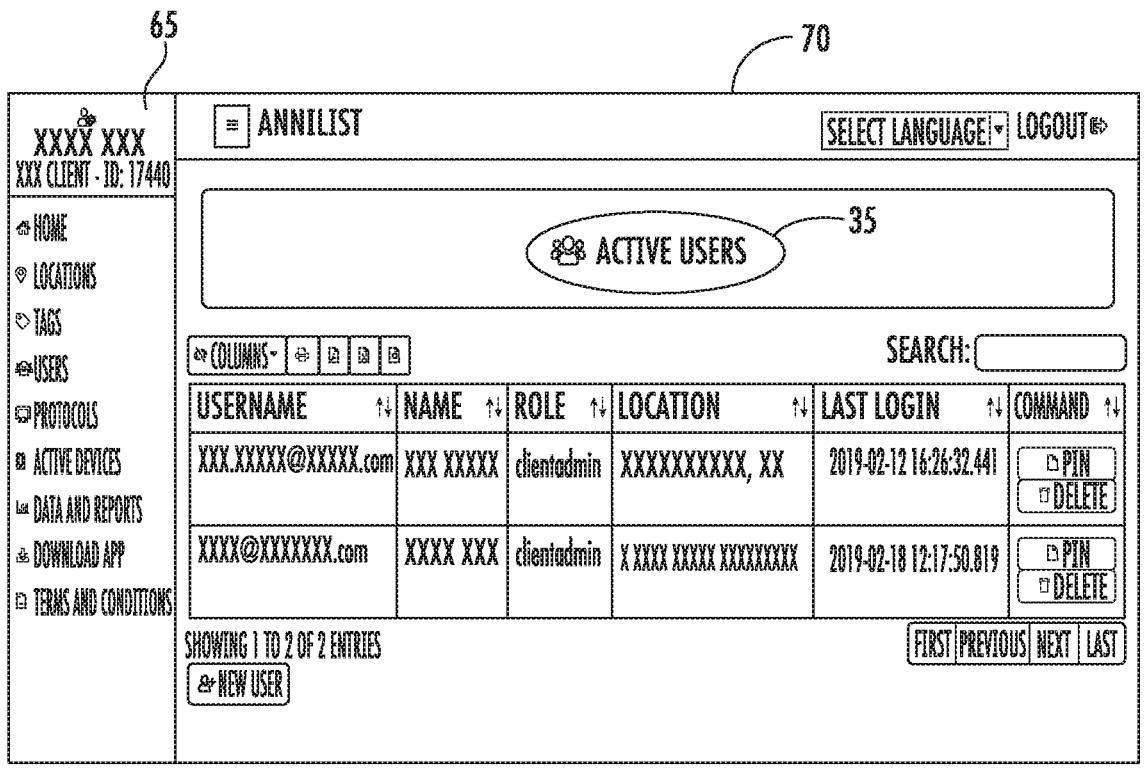
FIG. 8 shows a screenshot of the control panel of FIG. 7 displaying a listing of the active users of the system and method of FIG. 1.
Figure 9:
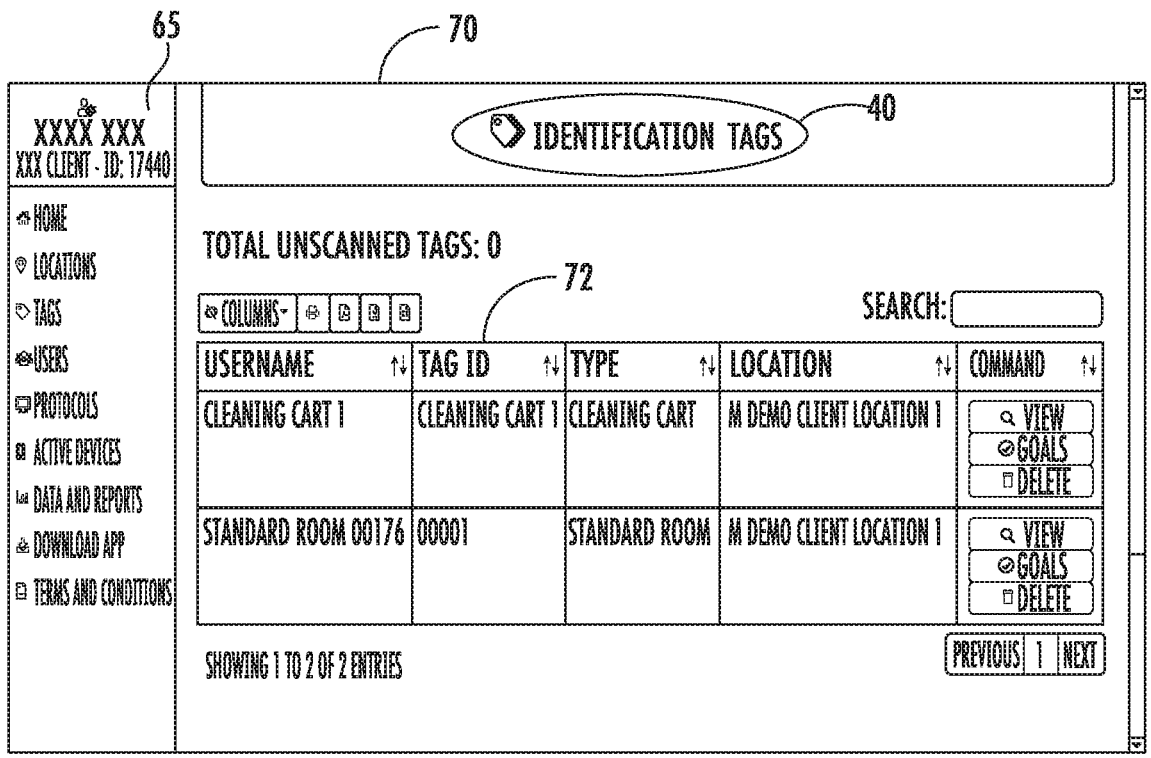
FIG. 9 shows a screenshot of the control panel of FIG. 7 displaying a listing of the identification tags of the system and method of FIG. 1.
Figure 10:
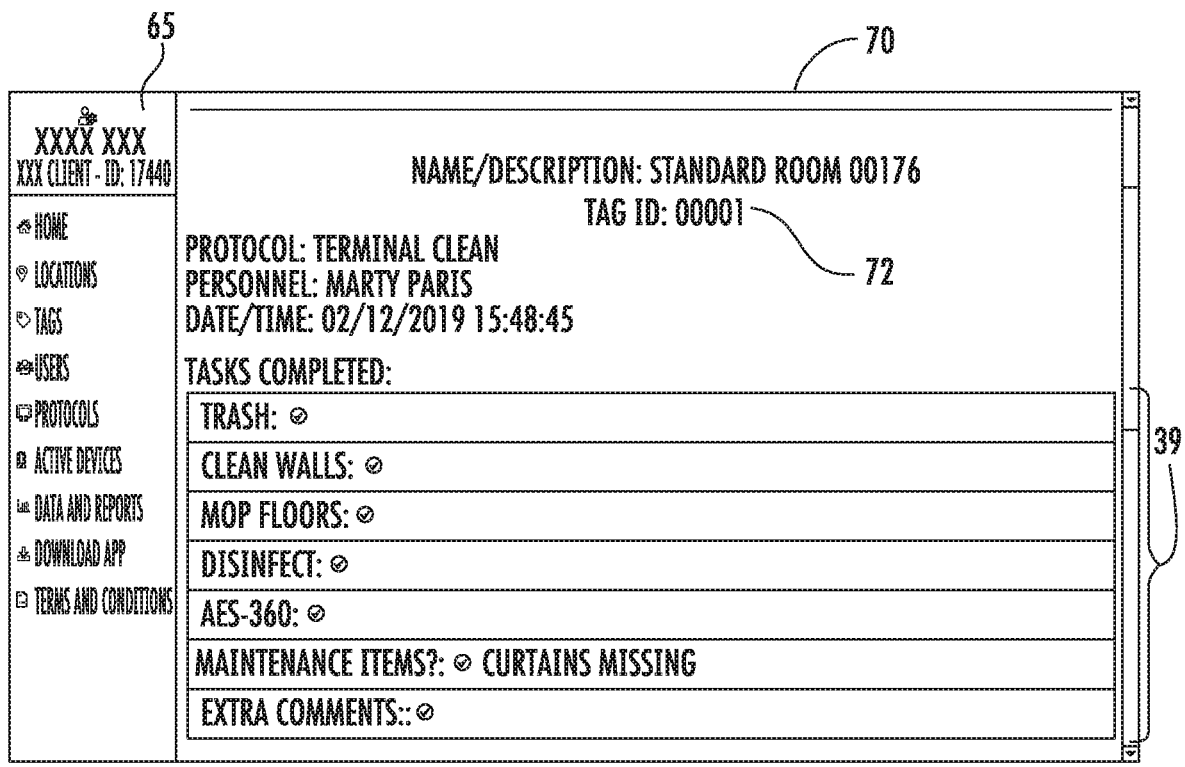
FIG. 10 shows a screenshot of the control panel of FIG. 7 displaying a check list of the instructions for a prescribed cleaning and disinfecting protocol of the system and method of FIG. 1.
Figure 11:
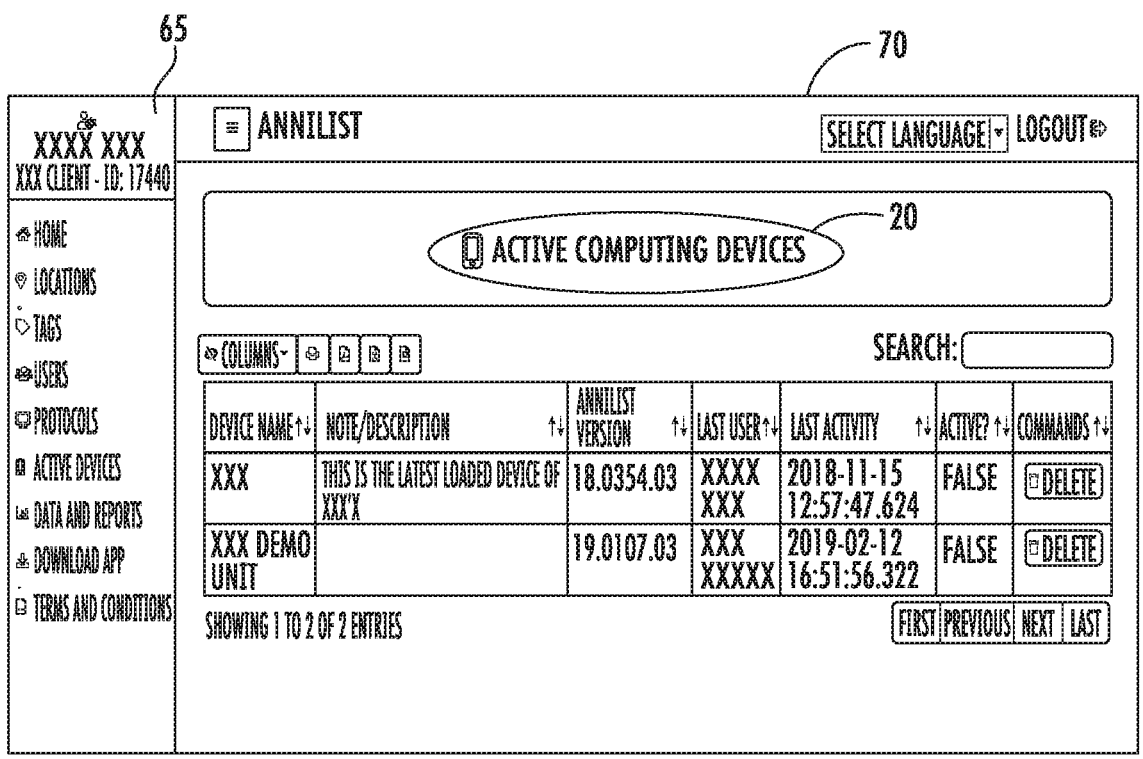
FIG. 11 shows a screenshot of the control panel of FIG. 7 displaying a listing of the portable computing devices of the system and method of FIG. 1.
Figure 12:
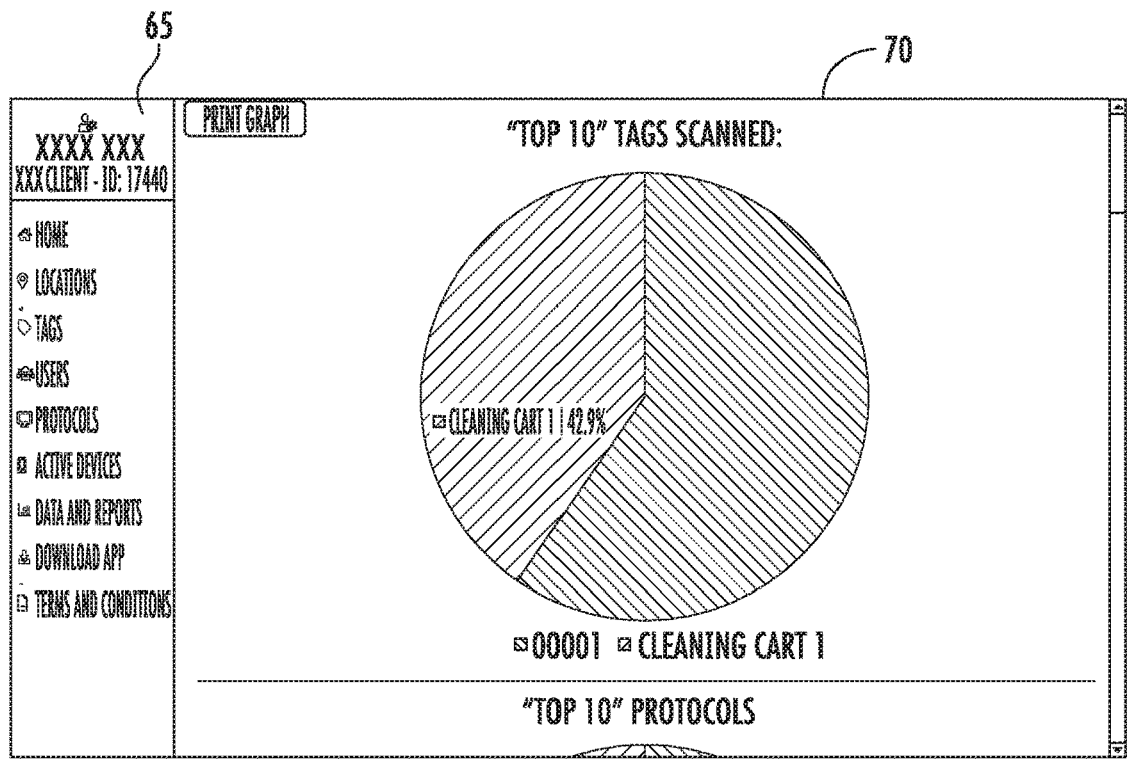
FIG. 12 shows a screenshot of the control panel of FIG. 7 displaying a first report of the system and method of FIG. 1.
Figure 13:
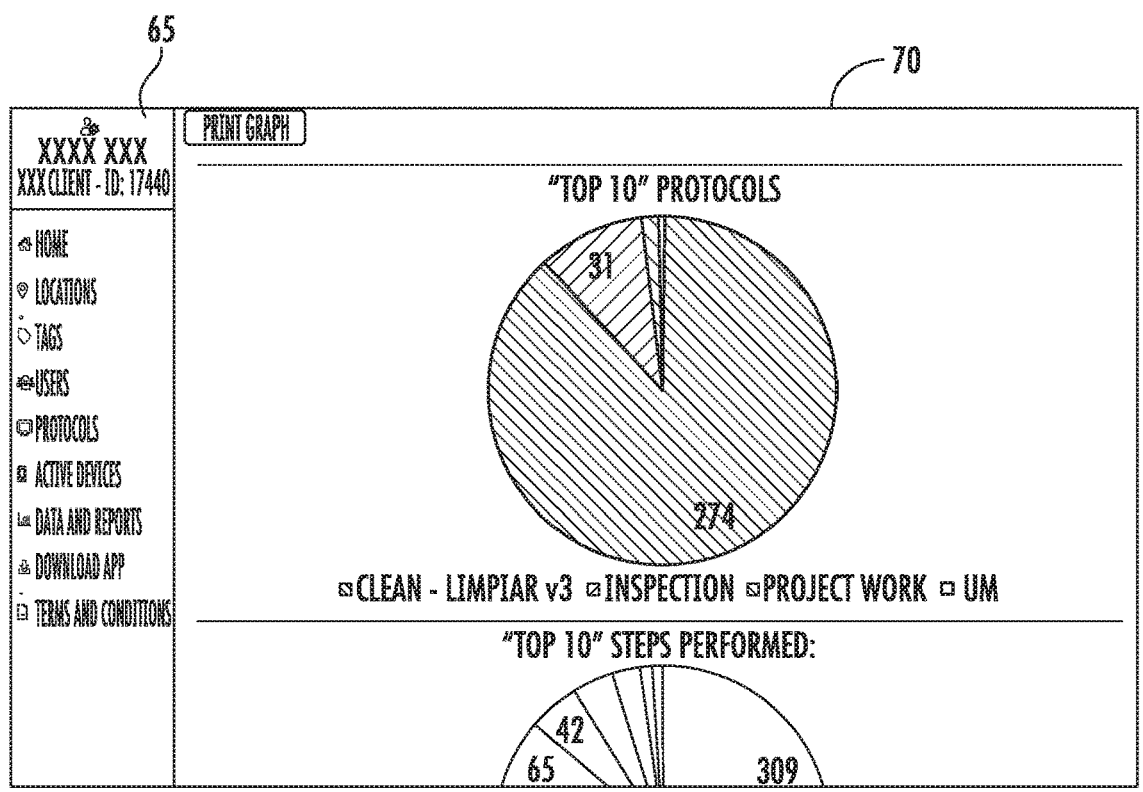
FIG. 13 shows a screenshot of the control panel of FIG. 7 displaying a second report of the system and method of FIG. 1.

A screenshot of an exemplary embodiment of a control panel 70 of the computer program 60 provided on the remote computing device 50 for use by an administrator 65 with the system 10 and method 100 of the present invention is shown in FIG. 7. FIG. 8 shows a screenshot of the control panel 70 displaying a listing of the active users 35 of the system 10 and method 100. The listing of active users 35 may include additional information, such as the location of the user 35 and the date and time the user 35 last logged into the portable computing device 20 and accessed the mobile app 30. FIG. 9 shows a screenshot of the control panel 70 displaying a listing of the identification tags 40 of the system 10 and method 100. The listing of identification tags 40 may include additional information, such as identification 72 for the identification tag 40 in the form of a unique name or a unique identification number. FIG. 10 shows a screenshot of the control panel 70 displaying a check list 39 of the instructions for a prescribed cleaning and disinfecting protocol 38 of the system 10 and method 100. FIG. 11 shows a screenshot of the control panel 70 displaying a listing of the active portable computing devices 20 of the system 10 and method 100. The listing of active computing devices 20 may include additional information, such as the date and time of the last activity of the portable computing device 20. FIG. 12 shows a screenshot of the control panel 70 displaying a first report of the system 10 and method 100. By way of example and not limitation, the first report depicts a pie chart of the "Top 10" identification tags 40 scanned by a portable computing device 20. FIG. 13 shows a screenshot of the control panel 70 displaying a second report of the system 10 and method 100. By way of example and not limitation, the second report depicts a pie chart of the "Top 10" cleaning and disinfecting protocols 38 performed.

The foregoing detailed description of exemplary embodiments of the system 10 and method 100 is merely illustrative of the general concept and principles of the present invention. Regardless of the foregoing description of exemplary embodiments, various other components and configurations of the system 10 and various other steps of the method 100 associated with the system 10, as well as reasonable equivalents thereof, will be readily apparent and understood by those skilled in the art. Accordingly, equivalent relationships to those shown in the accompanying drawing figures and described in the written description are intended to be encompassed by the broadest reasonable interpretation and construction of the appended claims. Furthermore, as numerous modifications and changes to the exemplary embodiments will readily occur to those skilled in the art, the present invention is not limited to the specific configuration, construction, materials, manner of use and operation shown and described herein. Instead, all reasonably predictable and suitable equivalents and obvious modifications to the invention should be determined to fall within the scope of the appended claims given their broadest reasonable interpretation and construction in view of the accompanying written description and drawing figures given the combined teachings of the disclosures of the relevant prior art.

That which is claimed is:

1. A system for performing a cleaning and disinfecting protocol and verifying the cleaning and disinfecting protocol was performed, comprising:
   a portable computing device operable for wireless communications and having a first machine-readable computer program resident on the portable computing device, the portable computing device comprising a processor for executing the first machine-readable computer program and a reader;
   at least one identification tag; and
   a remote computing device operable for wireless communications with the portable computing device and having a second machine-readable computer program resident on the remote computing device;
   wherein the reader of the portable computing device obtains information from the at least one identification tag comprising at least a unique identifier assigned to the identification tag; and
   wherein the remote computing device provides the cleaning and disinfecting protocol to the portable computing device for use with the first machine-readable computer program to perform the cleaning and disinfecting protocol based on the information obtained from the at least one identification tag and verifies that the cleaning and disinfecting protocol was performed.

2. The system according to claim 1, wherein the portable computing device comprises a near field communication (NFC) receiver for wirelessly receiving digital data from the at least one identification tag.

3. The system according to claim 1, wherein the portable computing device comprises a near field communication (NFC) transceiver for wirelessly receiving digital data from the at least one identification tag and wherein the at least one identification tag comprises a near field communication (NFC) transceiver for wirelessly transmitting the digital data to the portable computing device.

4. The system according to claim 1, wherein the at least one identification tag is operable for wirelessly receiving information in the form of digital data from the portable computing device.

5. The system according to claim 4, wherein the portable computing device and the at least one identification tag each comprise a near field communication (NFC) transceiver for receiving and/or transmitting information in the form of digital data.

6. The system according to claim 1, wherein the information from the at least one identification tag comprises the identity and/or the contents of a cleaning cart for use with the cleaning and disinfecting protocol.

7. The system according to claim 1, wherein the information from the at least one identification tag comprises the identity and/or the contents of a location to be cleaned and disinfected with the cleaning and disinfecting protocol.

8. The system according to claim 1, wherein the at least one identification tag is operable for wirelessly receiving information in the form of digital data and wherein the remote computing device provides the information in the form of digital data to the at least one identification tag.

9. The system according to claim 1,
   wherein the second machine-readable computer program on the remote computing device provides the first machine-readable computer program on the portable computing device by means of wireless communications between the remote computing device and the portable computing device; and
   wherein the portable computing device provides the information in the form of digital data to the at least one identification tag by means of wireless communications.

10. A method for performing a cleaning and disinfecting protocol and verifying the cleaning and disinfecting protocol was performed, comprising:
    providing a portable computing device operable for wireless communications and having a first machine-readable computer program resident on the portable computing device, the portable computing device comprising a processor for executing the first machine-readable computer program and a reader;
    providing at least one identification tag;
    using the reader of the portable computing device to obtain information from the at least one identification tag comprising at least a unique identifier assigned to the identification tag;
    providing a remote computing device operable for wireless communications with the portable computing device and having a second machine-readable computer program resident on the remote computing device, wherein the second machine-readable computer program on the remote computing device provides the cleaning and disinfecting protocol to the first machine-readable computer program on the portable computing device by means of wireless communications between the remote computing device and the portable computing device based on the information from the at least one identification tag;

utilizing the information obtained from the at least one identification tag with the first machine-readable computer program resident on the portable computing device to perform the cleaning and disinfecting protocol and with the second machine-readable computer program resident on the remote computing device to verify the cleaning and disinfecting protocol was performed.

11. The method according to claim 10, wherein the portable computing device comprises a near field communication (NFC) receiver for wirelessly receiving the information from the at least one identification tag.

12. The method according to claim 10, wherein the portable computing device comprises a near field communication (NFC) transceiver for wirelessly receiving the information from the at least one identification tag and wherein the at least one identification tag comprises a near field communication (NFC) transceiver for wirelessly transmitting the information to the portable computing device.

13. The method according to claim 10, wherein, the at least one identification tag is operable for wirelessly receiving information in the form of digital data from at least one of the portable computing device and the remote computing device.

14. A system for performing a cleaning and disinfecting protocol and for verifying that a prescribed cleaning and disinfecting protocol was performed, comprising:

a portable computing device operable for wireless communications and having a first machine-readable computer program resident on the portable computing device; and a remote computing device operable for wireless communications and having a second machine-readable computer program resident on the remote computing device; and at least one identification tag having information comprising at least a unique identifier assigned to the identification tag;

wherein the portable computing device obtains the information from the at least one identification tag; and wherein the first machine-readable computer program on the portable computing device provides the information from the at least one identification tag to the second machine-readable computer program on the remote computing device by means of wireless communications between the portable computing device and the remote computing device; and wherein the second machine-readable computer program on the remote computing device provides the prescribed cleaning and disinfecting protocol to the first machine-readable computer program on the portable computing device based on the information from the at least one identification tag; and wherein the second machine-readable computer program on the remote computing device verifies that the prescribed cleaning and disinfecting protocol was performed.

15. The system according to claim 14, wherein the portable computing device comprises a reader for obtaining the information in the form of digital data from the at least one identification tag.

16. The system according to claim 14, wherein the first machine-readable computer program on the portable computing device is a mobile app.

\* \* \* \* \*